United States Patent [19]

Wätjen et al.

[11] Patent Number: 5,198,461

[45] Date of Patent: Mar. 30, 1993

[54] ISATINE DERIVATIVES, THEIR PREPARATION AND USE

[75] Inventors: Frank Wätjen, Herlev; Jorgen Drejer, Vaerlose; Leif H. Jensen, Copenhagen V, all of Denmark

[73] Assignee: NeuroSearch A/S, Glostrup, Denmark

[21] Appl. No.: 710,790

[22] Filed: Jun. 5, 1991

Related U.S. Application Data

[63] Continuation-in-part of Ser. No. 624,409, Dec. 7, 1990, abandoned.

[30] Foreign Application Priority Data

| Dec. 11, 1989 | [DK] | Denmark | 6248/89 |
| Dec. 19, 1989 | [DK] | Denmark | 6470/89 |
| Jan. 12, 1990 | [DK] | Denmark | 0085/90 |
| Jan. 12, 1990 | [DK] | Denmark | 0086/90 |
| Feb. 12, 1990 | [DK] | Denmark | 0363/90 |
| Aug. 31, 1990 | [DK] | Denmark | 2093/90 |

[51] Int. Cl.$^5$ ............... C07D 209/62; A61K 31/40
[52] U.S. Cl. ................... 514/411; 514/418; 548/450; 548/483
[58] Field of Search ............ 548/450, 483; 514/411, 514/418

[56] References Cited

U.S. PATENT DOCUMENTS

| 3,897,434 | 7/1975 | Katner | 548/483 |
| 4,780,477 | 10/1988 | Kobayashi et al. | 514/418 |

FOREIGN PATENT DOCUMENTS 8903818  5/1989  World Int. Prop. O. .

*Primary Examiner*—Mary C. Lee
*Assistant Examiner*—Mary Susan H. Gabilan
*Attorney, Agent, or Firm*—Gordon W. Hueschen

[57] ABSTRACT

A method of treatment with compounds having the formula

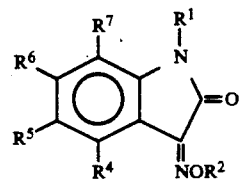

$R^1$ is hydrogen, $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$; $R^2$ is hydrogen, benzyl, $C_{1-6}$-alkyl which may be branched, or $C_{3-7}$-cycloalkyl; $R^4$, $R^5$, $R^6$, $R^7$ independently are hydrogen, $C_{1-6}$-alkyl which may be branched, phenyl, halogen, $C_{1-6}$-alkoxy, $NO_2$, CN, $CF_3$, $OCF_3$, or $SO_2NR''R'''$ wherein $R''$ and $R'''$ independently are hydrogen, aralkoxy, aralkyl, or $C_{1-6}$-alkyl; or $R^6$ and $R^7$ together form an additional 4 to 7 membered ring which may be aromatic or partial saturated and which may be substituted with halogen, $NO_2$, $CF_3$, CN, $OCF_3$, $SO_2NR''R'''$ wherein $R''$ and $R'''$ independently are hydrogen, aralkoxy, aralkyl, or $C_{1-6}$-alkyl, and $R^4$ and $R^5$ have the meanings set forth above, are disclosed, as well as pharmaceutical compositions thereof. Certain of the compounds are novel.

The compounds and pharmaceutical compositions containing the compounds are useful in the treatment of central nervous system disorders and especially conditions sensitive to excitatory amino acids.

16 Claims, No Drawings

ISATINE DERIVATIVES, THEIR PREPARATION AND USE

The present application is a continuation-in-part of our prior filed co-pending application Ser. No. 07/624,409, filed Dec. 7, 1990 now abandoned.

The present invention relates to a method of treatment with compounds having excitatory amino acid antagonizing properties, pharmaceutical compositions comprising such compounds, and to novel compounds having excitatory amino acid antagonizing properties and to the preparation of such compounds.

It is an object of the present invention to provide a method of treating diseases in mammals, including a human, by antagonizing an excitatory amino acid in such mammal.

A second object of the present invention is to provide novel pharmaceutical compositions useful for the treatment of diseases in mammals, including a human, acting by antagonizing an excitatory amino acid in such mammal.

A third object of the present invention is to provide novel compounds useful for the treatment of diseases in mammals, including a human, acting by antagonizing an excitatory amino acid in such mammal.

BACKGROUND OF THE INVENTION

It is well known from Wiss, Z. Ernst-Moritz-Arndt-Univ. Greifswald, Math.-nat.wiss. Reihe 35, 39–44 (1986) 4, Pharmazie 39, H.10, 713 (1984), Pharmazie 87, H.12, 858–861 (1982), Neuroscience Letters 107, 327–330 (1989), PCT patent application International Publication Number WO 89/03818, and Khim.-Farm.zh. 23(11), 1349–1352 (1989), that certain of the chemical entities comprised within the scope of method of treatment according to the present invention are known to possess biological activity.

SUMMARY OF THE INVENTION

The invention then, inter alia, comprises the following, alone or in combination:

A method of antagonizing the biological effects of an excitatory amino acid of a subject in need of such antagonization comprising the step of administering to said subject an effective excitatory amino acid antagonizing amount of an indole-2,3-dione-3-oxime compound having the formula

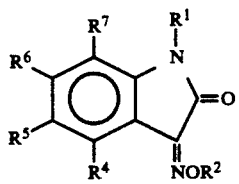

wherein $R^1$ is hydrogen, $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;

$R^2$ is hydrogen, benzyl, $C_{1-6}$-alkyl which may be branched, or $C_{3-7}$-cycloalkyl;

$R^4$, $R^5$, $R^6$, $R^7$ independently are hydrogen, $C_{1-6}$-alkyl which may be branched, phenyl, halogen, $C_{1-6}$-alkoxy, $NO_2$, $CN$, $CF_3$, $OCF_3$, or $SO_2NR''R'''$ wherein $R''$ and $R'''$ independently are hydrogen, aralkoxy, aralkyl, or $C_{1-6}$-alkyl; or $R^6$ and $R^7$ together form an additional 4 to 7 membered ring which may be aromatic or partial saturated and which may be substituted with halogen, $NO_2$, $CF_3$, $CN$, $OCF_3$, $SO_2NR''R'''$ wherein $R''$ and $R'''$ independently are hydrogen, aralkoxy, aralkyl, or $C_{1-6}$-alkyl, and $R^4$ and $R^5$ have the meanings set forth above, a method as above wherein at least one of $R^4$, $R^5$, $R^6$ or $R^7$ is an electron withdrawing substituent such as $NO_2$, $CF_3$, $CN$, $OCF_3$, $SO_2NR''R'''$, or halogen and $R^1$, $R^2$, $R^4$, $R^5$, $R^6$, $R^7$, $R''$, and $R'''$ otherwise have the meanings set forth, a method as first above wherein $R^5$ is $NO_2$, F, $CF_3$, $OCF_3$, or $CN$, moreover a method of antagonizing the biological effects of an excitatory amino acid as first above, wherein the compound is administered in the form of a pharmaceutical composition thereof, in which it is present together with a pharmaceutically acceptable carrier or diluent, and a method of antagonizing the biological effects of an excitatory amino acid as second above, wherein the compound is administered in the form of a pharmaceutical composition thereof, in which it is present together with a pharmaceutically acceptable carrier or diluent, further a pharmaceutical composition for use in antagonizing the biological effects of an excitatory amino acid of a subject in need of such antagonization comprising an effective excitatory amino acid antagonizing amount of a compound having the formula

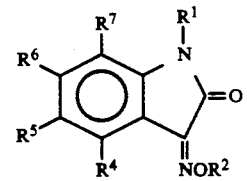

$R^1$ is hydrogen; $R^2$ is hydrogen, benzyl, $C_{1-6}$-alkyl which may be branched, or $C_{3-7}$-cycloalkyl;

$R^4$, $R^5$, $R^6$, $R^7$ independently are hydrogen, $C_{1-6}$-alkyl which may be branched, phenyl, halogen, $C_{1-6}$-alkoxy, $NO_2$, $CF_3$, $OCF_3$, $CN$, or $SO_2NR''R'''$ wherein $R'$ and $R'''$ independently are hydrogen, aralkoxy, aralkyl, or $C_{1-6}$-alkyl, or $R^6$ and $R^7$ together form an additional 4 to 7 membered ring which may be aromatic or partial saturated and which may be substituted with halogen, $NO_2$, $CF_3$, $CN$, $OCF_3$, $SO_2NR''R'''$ wherein $R''$ and $R'''$ independently are hydrogen, aralkoxy, aralkyl, or $C_{1-6}$-alkyl, and $R^4$ and $R^5$ have the meanings set forth above, at least one of $R^4$, $R^6$ and $R^7$ are other than hydrogen when $R^5$ is not other than H, Cl or Br;

or $R^1$ is $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, $CH_2C(=NOH)NH_2$;

$R_2$ is hydrogen, benzyl, $C_{1-6}$-alkyl which may be branched, or $C_{3-7}$-cycloalkyl;

$R^4$, $R^5$, $R^6$, $R^7$ independently are hydrogen, $C_{1-6}$-alkyl which may be branched, phenyl, halogen, $C_{1-6}$-alkoxy, $NO_2$, $CF_3$, $OCF_3$, $CN$, or $SO_2NR''R'''$ wherein $R''$ and R''' independently are hydrogen, aralkoxy, aralkyl, or $C_{1-6}$-alkyl, or $R^6$ and $R^7$ together form an additional 4 to 7 membered ring which may be aromatic or partial saturated and which may be substituted with halogen, $NO_2$, $CF_3$, CN, $OCF_3$, $SO_2NR''R'''$ wherein R'' and R''' independently are hydrogen, aralkoxy, aralkyl, or $C_{1-6}$-alkyl, and $R^4$ and $R^5$ have the meanings set forth above, at least one of $R^4$, $R^5$, $R^6$ and $R^7$ are other than hydrogen when $R^1$ is not other than methyl, at least one of $R^4$ and $R^5$ are other than hydrogen when $R^1$ is not other than phenyl which may be substituted, and at least one of $R^4$ and $R^5$ are other than hydrogen when $R^6$ and $R^7$ together form an additional benzene ring, and method of antagonizing the biological effects of an excitatory amino acid of a subject in need thereof comprising the step of administering to said subject a pharmaceutical composition as above, further a compound having the formula

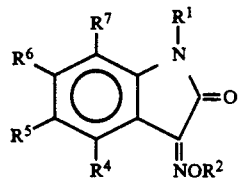

wherein $R^1$ is $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein R' is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$; $R^2$ is hydrogen, benzyl, $C_{1-6}$-alkyl which may be branched, or $C_{3-7}$-cycloalkyl;

$R^5$ is $NO_2$, F, CN, $OCF_3$, $CF_3$, or $SO_2NR''R'''$ wherein R'' and R''' independently are hydrogen, aralkoxy, aralkyl, or $C_{1-6}$-alkyl; and $R^4$, $R^6$, $R^7$ independently are hydrogen, $C_{1-6}$-alkyl which may be branched, phenyl, halogen, $C_{1-6}$-alkoxy, $NO_2$, $C_3$, $OCF_3$, CN, or $SO_2NR''R'''$ wherein R'' and R''' independently are hydrogen aralkoxy, aralkyl, or $C_{1-6}$-alkyl, or $R^6$ and $R^7$ together form an additional 4 to 7 membered ring which may be aromatic or partial saturated and which may be substituted with halogen, $NO_2$, $CF_3$, CN, $OCF_3$, $SO_2NR''R'''$ wherein R'' and R''' independently are hydrogen, aralkoxy, aralkyl or $C_{1-6}$-alkyl, $R^4$ has the meaning set forth above, and a compound having the formula

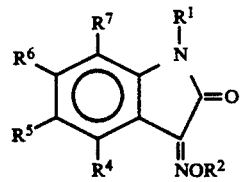

wherein $R^1$ is $C_{1-6}$-alkyl which may be branched, $C_{3-7}$-cycloalkyl, benzyl, acyl, hydroxy, $C_{1-6}$-alkoxy, $CH_2CO_2R'$ wherein R' is hydrogen or $C_{1-6}$-alkyl which may be branched, $CH_2CN$, $CO_2CONR^{IV}R^V$ wherein $R^{IV}$ and $R^V$ independently are hydrogen or $C_{1-6}$-alkyl, or $CH_2C(=NOH)NH_2$;

$R^2$ is hydrogen, benzyl, $C_{1-6}$-alkyl which may be branched, or $C_{3-7}$-cycloalkyl;

$R^5$ is $NO_2$, F, CN, $OCF_3$, $CF_3$, or $SO_2NR''R'''$ wherein R'' and R''' independently are hydrogen, aralkoxy, aralkyl or $C_{1-6}$-alkyl; and $R^4$, $R^6$, $R^7$ independently are hydrogen, $C_{1-6}$-alkyl which may be branched, phenyl, halogen, $C_{1-6}$-alkoxy, $NO_2$, $OCF_3$, $CF_3$, CN, or $SO_2NR''R'''$ wherein R'' and R''' independently are hydrogen, aralkoxy, aralkyl or $C_{1-6}$-alkyl, or $R^6$ and $R^7$ together form an additional 4 to 7 membered ring which may be aromatic or partial saturated and which may be substituted with halogen, $NO_2$, $CF_3$, CN, $OCF_3$, $SO_2NR''R'''$ wherein R'' and R''' independently are hydrogen, aralkyl, aralkoxy or $C_{1-6}$-alkyl; and and a compound having the formula

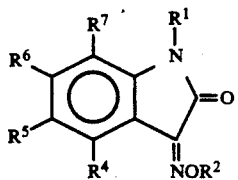

wherein
$R^1$ is hydrogen, $R^2$ is hydrogen, benzyl, $C_{1-6}$-alkyl which may be branched, or $C_{3-7}$-cycloalkyl; $R^5$ is $NO_2$, F, $CF_3$, CN, $OCF_3$, or $SO_2NR''R'''$ wherein R'' and R''' independently are hydrogen, aralkoxy, aralkyl or $C_{1-6}$-alkyl; and $R^4$, $R^6$, $R^7$ independently are hydrogen, $C_{1-6}$-alkyl which may be branched, phenyl, halogen, $C_{1-6}$-alkoxy, $NO_2$, $CF_3$, $OCF_3$, CN, or $SO_2NR''R'''$ wherein R'' and R''' independently are hydrogen, aralkoxy, aralkyl or $C_{1-6}$-alkyl, or $R^6$ and $R^7$ together form an additional 4 to 7 membered ring which may be aromatic or partial saturated and which may be substituted with halogen, $NO_2$, $CF_3$, CN, $OCF_3$, $SO_2NR''R'''$ wherein R'' and R''' independently are hydrogen, aralkyl, aralkoxy or $C_{1-6}$-alkyl, and $R^4$ has the meaning set forth above; and that $R^5$ is different from $NO_2$ and F when $R^1$, $R^4$, $R^6$ and $R^7$ are not other than hydrogen and $R^2$ is not other than hydrogen or benzyl; and that $R^5$ is different from $NO_2$ when $R^1$, $R^2$, $R^4$ and $R^6$ are not other than hydrogen and $R^7$ is not other than $NO_2$, further a compound as above wherein $R^4$ and $R^5$ independently are hydrogen, F, $NO_2$, CN, $CF_3$, $OCF_3$, or $SO_2NR''R'''$ wherein R'' and R''' independently are hydrogen, aralkoxy, aralkyl or $C_{1-6}$-alkyl, and wherein $R^6$ and $R^7$ together form an additional 4 to 7 membered ring which may be aromatic or partial saturated and which may be substituted with halogen, $NO_2$, $CF_3$, $OCF_3$, CN, $SO_2NR''R'''$ wherein R'' and R''' independently are hydrogen, aralkoxy, aralkyl or $C_{1-6}$-alkyl, and a compound as above wherein the additional ring formed by $R^6$ and $R^7$ is substituted with halogen, $NO_2$, $CF_3$, CN or $SO_2NR''R'''$ wherein R'' and R''' independently are hydrogen, aralkoxy, aralkyl or $C_{1-6}$-alkyl, and a compound as above, which is 6-(N-methylsulphamoyl)-5-nitro-1H-benz[g]indole-2,3-dione-3-oxime, and a compound as above, which is 5,7-dinitro-1-methyl-1H-indole-2,3-dione-3-(O-methyloxime), and a compound as above, which is 5-(N-benzyloxysulphamoyl)-1H-6,7,8,9-tetrahydro-benz[g]indole-2,3-dione-3-oxime, moreover, a method of treating a central nervous system disorder in a subject in need of such treatment, comprising the step of administering to said subject an effective amount of a compound having the formula

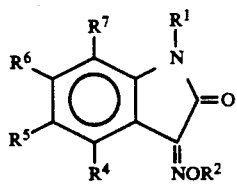

wherein $R^1$ is hydrogen, $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_{1-6}C(=NOH)NH_2$; $R^2$ is hydrogen, benzyl, $C_{1-6}$-alkyl which may be branched, or $C_{3-7}$-cycloalkyl;

$R^5$ is $NO_2$, F, $CF_3$, $OCF_3$, CN, or $SO_2NR''R'''$ wherein $R''$ and $R'''$ independently are hydrogen, aralkyl, aralkoxy or $C_{1-6}$-alkyl; and $R^4$, $R^6$, $R^7$ independently are hydrogen, $C_{1-6}$-alkyl which may be branched, phenyl, halogen, $C_{1-6}$-alkoxy, $NO_2$, CN, $CF_3$, $OCF_3$, or $SO_2NR''R'''$ wherein $R''$ and $R'''$ independently are hydrogen, aralkoxy, aralkyl or $C_{1-6}$-alkyl, or $R^6$ and $R^7$ together form an additional 4 to 7 membered ring which may be aromatic or partial saturated and which may be substituted with halogen, $NO_2$, $CF_3$, CN, $OCF_3$, $SO_2NR''R'''$ wherein $R''$ and $R'''$ independently are hydrogen, aralkoxy, aralkyl or $C_{1-6}$-alkyl, and $R^4$ has the meaning set forth above; and that $R^5$ is different from $NO_2$ and F when $R^1$, $R^4$, $R^6$ and $R^7$ are not other than hydrogen and $R^2$ is not other than hydrogen or benzyl; and that $R^5$ is different from $NO_2$ when $R^1$, $R^2$, $R^4$ and $R^6$ are not other than hydrogen and $R^7$ is not other than $NO_2$, further a method of preparing a compound having the formula

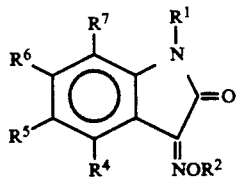

wherein $R^1$ is hydrogen, $C_{1-6}$-alkyl which may be branched, $C_{3-7}$-cycloalkyl, benzyl, phenyl which may be substituted, acyl, hydroxy, $C_{1-6}$-alkoxy; $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$; $R^2$ is hydrogen, benzyl, $C_{1-6}$-alkyl which may be branched, or $C_{3-7}$-cycloalkyl;

$R^5$ is $NO_2$, F, $CF_3$, CN, $OCF_3$, or $SO_2NR''R'''$ wherein $R''$ and $R'''$ independently are hydrogen, aralkoxy, aralkyl or $C_{1-6}$-alkyl; and $R^4$, $R^6$, $R^7$ independently are hydrogen, $C_{1-6}$-alkyl which may be branched, phenyl, halogen, $C_{1-6}$-alkoxy, $NO_2$, CN, $CF_3$, $OCF_3$, or $SO_2NR''R'''$ wherein $R''$ and $R'''$ independently are hydrogen, aralkoxy, aralkyl or $C_{1-6}$-alkyl, or $R^6$ and $R^7$ together form an additional 4 to 7 membered ring which may be aromatic or partial saturated and which may be substituted with halogen, $NO_2$, $CF_3$, CN, $OCF_3$, $SO_2NR''R'''$ wherein $R''$ and $R'''$ independently are hydrogen, aralkoxy, aralkyl or $C_{1-6}$-alkyl, and $R^4$ has the meaning set forth above; and that $R^5$ is different from $NO_2$ and F when $R^1$, $R^4$, $R^6$ and $R^7$ are not other than hydrogen and $R^2$ is not other than hydrogen or benzyl; and that $R^5$ is different from $NO_2$ when $R^1$, $R^2$, $R^4$ and $R^6$ are not other than hydrogen and $R^7$ is not other than $NO_2$, comprising the step of reacting a compound of the formula

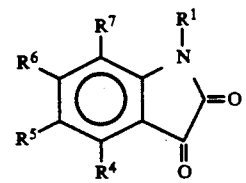

wherein $R^1$, $R^4$, $R^5$, $R^6$ and $R^7$ have the meanings set forth above, with a compound having the formula $NH_2OR^2$, wherein $R^2$ has the meaning set forth above, and moreover the use of a compound having the formula

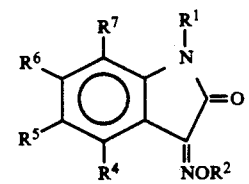

wherein $R^1$ is hydrogen, $C_{1-6}$-alkyl which may be branched, $C_{1-6}$-cycloalkyl, benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;

$R^2$ is hydrogen, benzyl, $C_{1-6}$-alkyl which may be branched, or $C_{3-7}$-cycloalkyl;

$R^4$, $R^5$, $R^6$, $R^7$ independently are hydrogen, $C_{1-6}$-alkyl which may be branched, phenyl, halogen, $C_{1-6}$-alkoxy, $NO_2$, $CN_2CF_3$, $OCF_3$, or $SO_2NR''R'''$ wherein $R''$ and $R'''$ independently are hydrogen, aralkoxy, aralkyl, or $C_{1-6}$-alkyl; or $R^6$ and $R^7$ together form an additional 4 to 7 membered ring which may be aromatic or partial saturated and which may be substituted with halogen, $NO_2$, $CF_3$, CN, $OCF_3$, $SO_2NR''R'''$ wherein $R''$ and $R'''$ independently are hydrogen, aralkoxy, aralkyl, or $C_{1-6}$-alkyl, and $R^4$ and $R^5$ have the meanings set forth above, for the preparation of a medicament useful in the treatment of conditions sensitive to an excitatory amino acid, and the use as above wherein at least one of $R^4$, $R^5$, $R^6$ or $R^7$ is an electron withdrawing substituent such as $NO_2$, $CF_3$, CN, $OCF_3$, $SO_2NR''R'''$, or halogen and $R^1$, $R^2$, $R^4$, $R^5$, $R^6$, $R^7$, $R''$ and $R'''$ otherwise have the meanings set forth above, and further a method of preparing a pharmaceutical preparation containing as active ingredient an effective amount of a compound having the formula

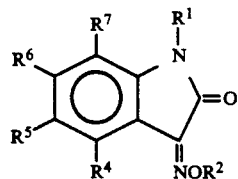

wherein $R^1$ is hydrogen, $C_{1-6}$-alkyl which may be branched, $C_{3-7}$-cycloalkyl, benzyl, phenyl which may be substituted, acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;

$R^2$ is hydrogen, benzyl, $C_{1-6}$-alkyl which may be branched, or $C_{3-7}$-cycloalkyl;

$R^4$, $R^5$, $R^6$, $R^7$ independently are hydrogen, $C_{1-6}$-alkyl which may be branched, phenyl, halogen, $C_{1-6}$-alkoxy, $NO_2$, $CN$, $CF_3$, $OCF_3$, or $SO_2NR''R'''$ wherein $R''$ and $R'''$ independently are hydrogen, aralkoxy, aralkyl, or $C_{1-6}$-alkyl; or $R^6$ and $R^7$ together form an additional 4 to 7 membered ring which may be aromatic or partial saturated and which may be substituted with halogen, $NO_2$, $CF_3$, $CN$, $OCF_3$, $SO_2NR''R'''$ wherein $R''$ and $R'''$ independently are hydrogen, aralkoxy, aralkyl or $C_{1-6}$-alkyl, and $R^4$ and $R^5$ have the meanings set forth above.

Biological Activity

The compounds of the invention exhibit valuable biological properties because of their strong excitatory amino acid (EAA) (glycine, glutamate, quisqualate, ATPA, AMPA, kainate, NMDA) antagonizing properties.

For example compounds of the invention exhibit strong pharmacological in vivo ATPA and quisqualate antagonizing effects demonstrating their utility as novel orally-bioavailable excitatory amino acid antagonists, which makes them useful in the treatment of for example excitatory amino acid dependent psychosis, excitatory amino dependent anoxia, excitatory amino acid dependent ischemia, excitatory amino acid dependent convulsions, and excitatory amino acid dependent migraine.

Compounds of the invention will inhibit ATPA-induced rigidity and quisqualate or NMDA-induced convulsions with an $ED_{50}$ in the range of 0.1-10.0 mg/kg. Examples of such compounds are 5,7-dinitro-1-methyl-1H-indole-2,3-dione-3-(O-methyloxime) and 5,7-dinitro-1-(ethoxy carbonyl methyl)-1H-indole-2,3-dione-3-(O-methyloxime).

Compounds of the invention show potent in vitro affinity for the glutamate subreceptors kainate, quisqualate and glycine receptors. These properties make the compounds useful in the treatment of human malfunctions related to the excitatory amino acids (EAA).

For example some compounds of the invention exhibit binding at the $^3$H-kainate, $^3$H-AMPA and/or $^3$H-glycine binding sites with $IC_{50}$ in the range of 10-100 $\mu$M. Examples of such compounds are for example
5-bromo-7-nitro-1H-indole-2,3-dione-3-oxime,
5-nitro-1H-indole-2,3-dione-3-oxime,
5,7-dinitro-1H-indole-2,3-dione-3-oxime,
5,7-dinitro-1-methyl-1H-indole-2,3-dione-3-oxime,
1H-benz[g]indole-2,3-dione-3-oxime,
5-nitro-1H-benz[g]indole-2,3-dione-3-oxime,
5-nitro-1H-6,7,8,9-tetrahydro-benz[g]indole-2,3-dione-3-oxime.
5-(N-methylsulphamoyl)-6,7,8,9-tetrahydro-1H-benz[g]indole-2,3-dione-3-oxime, and
5-(benzyloxysulphamoyl)-6,7,8,9-tetrahydro-1H-benz[g]indole-2,3-dione-3-oxime Also the compounds of the invention as a secondary result of their EAA-antagonizing properties have been found to antagonize cocaine-induced hypermotility. For example the most potent compounds of the invention have been found to have an $ED_{50}$ in the range of 0.5-1.0 mg/kg in this test when administered orally. An example of such a compound is 5,7-dinitro-1-methyl-1H-indole-2,3-dione-3-(O-methyloxime).

Furthermore it has been found that some of the compounds of the invention are metabolites of other compounds of the invention and that the metabolites exhibit biological activity in the same range or are even more potent than the precursor compounds of the invention. Accordingly both such parent or precursor compounds and such metabolites fall within the scope of the invention. Some of the compounds named in the foregoing will be recognized as metabolites of precursor compounds named in the foregoing, and vise versa.

Such metabolites are for example:
N-dealkylated derivatives, 1-N-hydroxyalkyl derivatives, 1-N-hydroxy derivatives, 1-N-oxide derivatives, O-dealkylated derivatives, pyrrolo ring opened hydrolyzed derivatives, pyrrolo ring opened hydrolyzed and decarboxylated derivatives as well as combinations of such metabolisation reactions.

Biological testing

The above mentioned tests are performed as described in more detail below and are based upon the principles also described hereinafter.

ATPA-induced rigidity

The selective quisqualate receptor agonist ATPA induces rigidity in female NMRI mice at doses between 3 and 15 mg/kg and clonic-tonic seizures and death, probably due to respiratory arrest, at doses between 15 and 40 mg/kg after intravenous (i.v.) administration.

Method

ATPA ((RS)-α-amino-3-hydroxy-5-tert-butyl-4-isoxazolepropionic acid) was dissolved in distilled water and test compound was dissolved in a polyoxyl 40 hydrogenated castor oil (5% Cremophor RH ™ 40 (BASF)).

Test compound was administered either i.v. 5, 30 or 120 min before or p.o. 30 min before an i.v. administration of 15 mg/kg of ATPA to 8 female NMRI mice per dose and the number of mice experiencing rigidity 5 min later was noted. An $ED_{50}$ value was calculated from at least three doses of test compound as the dose inhibiting 50% of the mice from having rigidity.

Quiscualate-induced clonic seizures

Quisqualate given icv (intracerebroventricular) to DBA/2 mice induces clonic seizures which can be inhibited by both NMDA and non-NMDA receptor antagonists after i.v. administration.

Method

Test compound was given i.v. 5 min before a 20 pg icv administration of quisqualate to 10 male DBA/2 mice (weighing 10-12 g) per dose. The number of mice experiencing clonic seizures within the next 2 min was noted. An $ED_{50}$ value was calculated as the dose inhibiting 50% of the mice from having clonic seizures.

NMDA-induced clonic seizures

NMDA give icv to NMRI mice induces clonic seizures which can be inhibited by NMDA receptor antagonists.

Method

Test compound was given i.v. 5 min before a 0.5 μg icv administration of NMDA to 10 male NMRI mice per dose. The number of mice experiencing clonic seizures within the next 2 min was noted. An $ED_{50}$ value was calculated as the dose inhibiting 50% of the mice from having clonic seizures.

Cocaine-induced hypermotility

Quisqualate and kainate administered locally induce an increase in dopamine release in nucleus accumbens and nucleus caudatus accompanied by stereotype behaviour such as hyperlocomotion, rearing, sniffing and grooming. These effects can be inhibited by selective quisqualate antagonists administered locally by the micro-dialyses method.

Also the dopamine uptake inhibitor cocaine administered s.c. induce hypermotility which can be inhibited by an administration of the glutamate antagonist GDEE into nucleus accumbens.

For these reasons (and others) it has been concluded that non-NMDA receptors regulate the release of dopamine in nucleus accumbens and that non-NMDA receptor antagonists can alleviate the symptoms of psychosis.

Method

Test compound was administered orally at doses of 0.1, 1, 10 and 30 mg/kg 30 min before the administration of 25 mg/kg cocaine i.p. to female NMRI mice and the locomotor activity of 2 mice per box was measured for the next 2 hours by use of 8 infrared photobeams per box. The mice had been adapted to the box for at least 16 hours to avoid exploratory motility (neophobia).

The quisqualate binding assay was performed as described by T. Honoré et al., Neuroscience Letters 54, 27-32 (1985).

The kainate binding assay was performed as described by T. Honoré et al., Neuroscience Letters 65, 47-52 (1986).

The glycine binding assay was performed as described by W. Frost White et al., Journal of Neurochemistry 53(2), 503-512 (1989).

Pharmaceutical Compositions

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) milligrams of active ingredients or, more broadly, 0.1 to one hundred (100) milligrams, per tablet, are accordingly suitable representative unit dosage forms.

Solid forms of pharmaceutical compositions for p.o. administration and injectable solutions are preferred.

Method of Treating

The compounds of this invention are extremely useful in the treatment of central nervous system disorders related to their biological activity. The compounds of this invention may accordingly be administered to a subject, including a human, in need of treatment, alleviation, or elimination of an indication associated with the biological activity of the compounds. This includes especially excitatory amino acid dependent psychosis, excitatory amino acid dependent anoxia, excitatory amino acid dependent ischemia, excitatory amino acid dependent convulsions and excitatory amino acid dependent migraine. Suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

Chemical Examples

Some compounds of the invention are old, and others are novel chemical entities. In any-way the compounds of the invention may be prepared according to chemical methods which are well known.

EXAMPLE 1 a) 1-phenyl-1H-indole-2,3-dione.

To a stirred solution of diphenylamine (3.2 g, 20 mmol) and 4-dimethylaminopyridine (10 mg) in chloroform (50 ml) was dropwise added oxalylchloride (3 ml). The resulting mixture was refluxed for 5 hours, whereafter it was cooled to room temperature and evaporated in vacuo.

The residue (oil) was redissolved in methylene chloride (50 ml) and dry $AlCl_3$ (3 g) was added. Stirring at room temperature was continued for 30 hours, whereafter ethanol (10 ml) followed by water (100 ml) were added. The organic phase was washed with saturated $Na_2CO_3$, dried over $Na_2SO_4$ and evaporated. The crystalline residue was stirred in ether (40 ml) and the product was filtered off. Yield: 2.65 g orange crystals, M.p. 139°-141° C., litt. 138° C.

b) The following 1H-indole-2,3-diones were prepared from the corresponding anilines or naphthyl amines according to known literature procedures.

1)Organic Synthesis Col Vol. I p. 327.

hu 2)Martinet, J.: Compt. Rend. 166, 851, 1918.

4,6-ditrifluoromethyl-1H-indole-2,3-dione[1], M.p. 162°-165° C.

1H-benz[g]indole-2,3-dione[2], M.p. 242°-245° C.

6-sulphamoyl-1H-benz[g]indole-2,3-dione, [1] M.p.>350° C.

6-(N-burtylsulphamoyl)-1H-benz[g]indole-2,3-dione [1] M.p. 282°-285° C.

5-trifluoromethoxy-1H-indole-2,3-dione, [1] M.p. 160°-161° C.

6-(N-methylsulphamoyl-1H-benz[g]indole-2,3-dione, [1)] M.p.>300° C.

7-trifluoromethyl-1H-indole-2,3-dione[1)], M.p. 181°-183° C.

1H-6,7,8,9-tetrahydro-benz[g]indole-2,3-dione, M.p. 224°-226° C.

6-methoxy-1H-indole-2,3-dione, M.p. >310° C.

7-trifluoromethyl-1H-indole-2,3-dione, M.p. 180°-184° C.

c) 1-methyl-5-nitro-7-trifluoromethyl-1H-indole-2,3-dione.

To a stirred 10° C. warm solution of KNO₂ (0.5 g) in 10 ml of conc. H₂SO₄ was dropwise added a solution of 1-methyl-7-trifluoromethyl-1H-indole-2,3-dione in 10 ml of conc. H₂SO₄. The addition was completed after 10 min, whereafter stirring was continued for 15 min at room temperature. The reaction mixture was poured on ice whereby the title compound precipitated as yellow crystals. The crystals were collected by filtration and washed with water. M.p. 168°-169° C.

In a similar manner to c), the following nitro compounds were prepared:

6-(N-methylsulphamoyl)-5-nitro-1H-benz[g]indole-2,3-dione M.p. 220°-240° C. decomp.

5-nitro-1H-6,7,8,9-tetrahydro-benz[g]indole-2,3-dione, M.p. 232°-236° C.

5-nitro-1-methyl-1H-benz[g]indole-2,3-dione, M.p. 255°-258° C.

d) 5-sulphamoyl-1H-indole-2,3-dione.

1H-indole-2,3-dione(1.0 g, 6.8 mmol) was added in portions at room temperature to chlorosulphonic acid (4 ml, stirred). Stirring was continued at 50° C. for 30 min. The resulting reaction mixture was added dropwise onto crushed ice (50 g). The ice was allowed to melt, whereafter the precipitated sulphonylcloride was filtered off.

The crude product was added to a 25% solution of ammonia in water at 0° C. The solution was stirred at room temperature for 30 min., and thereafter evaporated in vacuo. The residue was acidified with hydrochlorid acid (4N). This treatment left the title compound as yellow crystals which was filtered off. The compound could be purified by SiO₂ cromatography or recrystallization from alcohols. M.p. 265°-66° C. in a similar manner were prepared the following compounds using the appropriate indoles and amines or hydroxylamines.

5-bromo-7-sulphamoyl-1H-indole-2,3-diones M.p. 233°-238° C.

5-sulphamoyl-6,7,8,9-tetrahydro-1H-benz[g]indole-2,3-dione M.p. >350° C.

5-(N-dimethylsulphamoyl)-1H-indole-2,3-dione M.p. 220°-224° C.

5-(N-benzylphamoyl)-6,7,8,9-tetrahydro-1H-benz[g]indole-2,3-dione M.p.>300° C.

5-(N-methylsulphamoyl)-6,7,8,9-tetrahydro-1H-benz[g]indole-2,3-dione M.p. 205°-210° C.

5-(N-benzyloxysulphamoyl)6,7,8,9-tetrahydro-1H-benz[g]indole-2,3-dione M.p.197°-200° C.

e) 5,7-dinitro-1-methyl-1H-indole-2,3-dione.

To a stirred solution of 5,7-dinitro-1H-indole-2,3-dione (1.2 g) in dry dimethylformamide (20 ml) was added sodium hydride (0.24 g 55% in mineral oil). After the hydrogen evolution had ceased methyl iodide (0.37 ml) was added. Stirring at room temperature was continued for 2 hours, whereafter the crude product was precipitated as an oil by addition of water (100 ml) to the reaction mixture. The oil crystallized upon treatment with ether/pentane, M.p. 154°-157° C.

In a similar manner to d), the following 1-alkyl- or 1-benzyl-1H-indole-2,3-diones were prepared.

5,7-dinitro-1-ethyl-1H-indole-2,3-dione, M.p. 135°-140° C.

5-bromo-1-methyl-1H-indole-2,3-dione, M.p. 157°-160° C.

1H-1-methyl-6,7,8,9-tetrahydro-benz[g]indole-2,3-dione, M.p. 157°-160° C.

5,7-dibromo-1-methyl-1H-indole-2,3-dione, M.p. 170°-173° C.

5,6-dichloro-1-methyl-1H-indole-2,3-dione, M.p. 180°-184° C.

4,5-dichloro-1-methyl-1H-indole-2,3-dione, M.p. 237°-239° C.

1-methyl-5-nitro-1H-indole-2,3-dione, M.p. 196°-199° C.

1-benzyl-5,7-dinitro-1H-indole-2,3-dione, M.p. 127°-131° C.

4,6-ditrifluoromethyl-1-methyl-1H-indole, M.p. 93°-94° C.

1-methyl-7-trifluoromethyl-1H-indole-2,3-dione, M.p. 120°-122° C.

6-methoxy-1-methyl-1H-indole-2,3-dione, M.p. 175°-178° C.

5,7-dinitro-1-(ethoxycarbonylmethyl)-1H-indole-2,3-dione, (oil).

1-methyl-1H-benz[g]indole-2,3-dione, M.p. 122°-126° C.

1-(ethoxycarbonylmethyl)-1H-indole-2,3-dione, M.p. 115°-119° C.

5,7-dibromo-1-(ethoxycarbonylmethyl)-1H-indole-2,3-dione, M.p. 97°-102° C.

1-methyl-1H-6,7,8,9-tetrahydrobenz[g]indole-2,3-dione, M.p. 160°-165° C.

EXAMPLE 2

5,7-dinitro-1-methyl-1H-indole-2,3-dione-3-(O-methyloxime). 5,7-dinitro-1-methyl-1H-indole-2,3-dione (0.4 g), O-methylhydroxylamine, hydrochloride (0.16 g) and sodium carbonate (0.2 g) was stirred at room temperature in ethanol (5 ml) for one hour, whereafter acetic acid (0.5 ml) followed by water (50 ml) were added. The mixture was cooled on ice and the crystalline product was obtained by filtration, M.p. 145°-151° C.

The following O-alkyloximes were prepared in a similar manner starting from the appropriate indole-2,3-diones.

5,7-dinitro-1H-indole-2,3-dione-3-(O-methyloxime), M.p. 236°-239° C.

5,7-dinitro-1-ethyl-1H-indole-2,3-dione-3-(O-methyloxime), M.p. 156°-159° C.

5-nitro-3-(O-methyloxime)-1H-indole-2,3-dione, M.p. 293°-295° C.

1-phenyl-1H-indole-2,3-dione-3-(O-methyloxime), M.p. 151°-153° C.

1H-indole-2,3-dione-3-(O-methyloxime), M.p. 168°-171° C.

5,7-dibromo-1-methyl-1H-indole-2,3-dione-3-(O-methyloxime), M.p. 170°-172° C.

5,7-dibromo-1H-indole-2,3-dione-3-(O-methyloxime), M.p. 279° C. (decomp.).

1-methyl-5-nitro-1H-indole-2,3-dione-3-(O-methyloxime), M.p. 167°-170° C.

5,6-dichloro-1-methyl-1H-indole-2,3-dione-3-(O-methyloxime), M.p. 202°-204° C.

4,5-dichloro-1-methyl-1H-indole-2,3-dione-3-(O-methyloxime), M.p. 180°-183° C.

5,7-dinitro-1-benzyl-1H-indole-2,3-dione-3-(O-methyloxime), M.p. 181°-185° C.

4,6-ditrifluoromethyl-1-methyl-1H-indole-2,3-dione-3-(O-methyloxime), M.p. 99°-100° C.

5-nitro-7-trifluoromethyl-1-methyl-1H-indole-2,3-dione-3-(O-methyloxime), M.p. 160°-161° C.

5-nitro-7-trifluoromethyl-1H-indole-2,3-dione-3-(O-methyloxime), M.p. 225°-228° C.

5,7-dinitro-6-methoxy-1-methyl-1H-indole-2,3-dione-3-(Omethyloxime), M.p. 145°-148° C.

5,7-dinitro-1-(O-ethylcarboxymethyl)-1H-indole-2,3-dione-3-(O-methyloxime), M.p. 115°-117° C.

5-nitro-1-methyl-1H-benz[g]indole-2,3-dione-3-(O-methyloxime), M.p. 255°-258° C.

5-bromo-1-(ethoxycarbonylmethyl)-1H-indole-2,3-dione-3-(O-methyloxime), M.p. 201°-204° C.

5,7-dibromo-1-(ethoxycarbonylmethyl)-1H-indole-2,3-dione-3-(O-methyloxime), M.p. 137°-138° C.

5-methyl-1-(methoxycarbonylmethyl)-1H-indole-2,3-dione-3-(O-methyloxime), M.p. 127°-131° C.

5-nitro-1-methyl-1H-6,7,8,9-tetrahydro-benz[g]indole-2,3-dione-3-(O-methyloxime), M.p. 220°-224° C.

Substitution of O-methyl-hydroxylamine hydrochloride in the process by hydroxylamine hydrochloride, afforded the following oximes.

1H-benz[g]indole-2,3-dione-3-oxime, M.p. 248°-250° C.

5,7-dinitro-1-methyl-1H-indole-2,3-dione-3-oxime, M.p. 244° C. (decomp.).

5,7-dibromo-1H-indole-2,3-dione-3-oxime, M.p. 240°-242° C.

5-bromo-1-methyl-1H-indole-2,3-dione-3-oxime, M.p. 213°-215° C.

5,7-dinitro-1H-indole-2,3-dione-3-oxime, M.p. 240°-242° C.

5-bromo-7-nitro-1H-indole-2,3-dione-3-oxime, M.p. 254°-256° C.

5-bromo-1H-indole-2,3-dione-3-oxime, M.p. 250°-251° C.

5-nitro-1H-indole-2,3-dione-3-oxime, M.p. 243°-245° C.

5-methyl-1H-indole-2,3-dione-3-oxime, M.p. 203°-206° C.

1H-indole-2,3-dione-3-oxime, M.p. 234°-236° C.

1-methyl-6,7,8,9-tetrahydro-1H-benz[g]indole-2,3-dione-3-oxime, M.p. 230°-232° C.

5,6-dichloro-1-methyl-1H-indole-2,3-dione-3-oxime, M.p. 232°-236° C.

4-phenyl-7-methoxy-1H-indole-2,3-dione-3-oxime, M.p. 201°-204° C.

4,5-dichloro-1H-indole-2,3-dione-3-oxime, M.p. 245°-247° C.

1-phenyl-1H-indole-2,3-dione-3-oxime, M.p. 166°-170° C.

4,5-dichloro-1-methyl-1H-indole-2,3-dione-3-oxime, M.p. 140°-142° C.

5-nitro-1H-benz[g]indole-2,3-dione-3-oxime, M.p. 197°-199° C.

5-nitro-7-trifluoromethyl-1-methyl-1H-indole-2,3-dione-3-oxime, M.p. 204°-205° C.

5-nitro-7-trifluoromethyl-1H-indole-2,3-dione-3-oxime, M.p. 230°-232° C.

5-nitro-1H-6,7,8,9-tetrahydro-benz[g]indole-2,3-dione-3-oxime, M.p. 205°-210° C.

5-fluoro-7-nitro-1H-indole-2,3-dione-3-oxime, M.p. 260°-262° C.

5,7-dinitro-1-(ethoxycarbonylmethyl)-1H-indole-2,3-dione-3-oxime, M.p. 217°-220° C.

1-(ethoxycarbonylmethyl)-1H-indole-2,3-dione-3-oxime, M.p. 183°-185° C.

5-bromo-1-(ethoxycarbonylmethyl)-1H-indole-2,3-dione-3-oxime, M.p. 178°-181° C.

5,7-dinitro-1H-indole-2,3-indole-2,3-dione-3-oxime, M.p. 195°-197° C.

6-sulphamoyl-1H-benz[g]indole-2,3-dione-3-oxime M.p. 286°-288° C.

6-(N-butylsulphamoyl)-1H-benz[g]indole-2,3-dione-3-oxime M.p. 200° C. dec.

5-trifluoromethoxy-1H-indole-2,3-dione-3-oxime M.p. 299-245.

5-sulphamoyl-1H-indole-2,3-dione-3-oxime M.p. 230°-233° C.

5-bromo-7-sulphamoyl-1H-indole-2,3-dione-3-oxime M.p. 269°-271° C.

6,7,8,9-tetrahydro-5-sulphamoyl-1H-benz[g]indole-3-oxime M.p. >350° C.

5-(n-dimethylsulphamoyl)-1H-indole-2,3-dione-3-oxime M.p. 198°-200° C.

5-(N-benzylsulphamoyl)-6,7,8,9-tetrahydro-1H-benz[g]indole-3-oxime M.p. 237°-239° C.

5-(N-methylsulphamoyl)-6,7,8,9-tetrahydro-1H-benz[g]indole-2,3-dione-3-oxime M.p. 255°-257° C.

5-(N-benzyloxysulphamoyl)-6,7,8,9-tetrahydro-1H-benz[g]indole-2,3-dione-3-oxime M.p. 248°-249° C.

6-(N-methylsulphamoyl)-5-nitro-1H-benz[g]indole-2,3-dione-3-oxime M.p. 246°-247° C.

5-trifluoromethoxy-1H-indole-2,3-dione-3-oxime M.p. 257°-258° C.

Substitution of hydroxylamine hydrochloride in the process by O-benzylhydroxylamine, afforded the following compounds.

5,7-dinitro-1H-indole-2,3-dione-3-(O-benzyloxime), M.p. 197°-199° C.

5,7-dinitro-1H-1-benzyl-indole-2,3-dione-3-(O-benzyloxime), M.p. 148°-150° C.

5,7-dinitro-1-methyl-1H-indole-2,3-dione-3-(O-benzyloxime), M.p. 120°-125° C.

5,7-dinitro-1-(ethoxycarbonylmethyl)-1H-indole-2,3-dione-3-(O-benzyloxime), M.p. 100°-102° C.

5-nitro-1-(ethoxycarbonylmethyl)-1H-indole-2,3-dione-3-(O-benzyloxime), M.p. 185°-187° C.

The following compounds were prepared according to literature procedures:

1-methoxy-1H-indole-2,3-dione-3-oxime, M.p. 166°-168° C.[1];

1-acetyl-5-bromo-1H-indole-2,3-dione, M.p. 133°-135° C.

1-hydroxy-1H-indole-2,3-dione-3-oxime, M.p. 217°-221° C.[1];

[1]A. Reiszert, Ber. vol. 41, 3921.

EXAMPLE 3 a) 1-carboxymethyl-1H-indole-2,3-dione.

8.39 g (36 mmol) 1-(ethoxycarbonylmethyl)-1H-indole-2,3-dione and 4N NaOH (10 ml, 40 mmol) were dissolved in 30 ml H$_2$O and 10 ml absolute ethanol and the mixture was heated at reflux for 30 minutes. The reaction mixture was cooled and added excess hydrochloric acid. The precipitate was isolated. Yield of title compound is 6.2 g.

b) 1-chlorocarbonylmethyl-1H-indole-2,3-dione.

1 g of the product prepared under a) was suspended in toluene (10 ml) and SOCl$_2$ (1.0 ml, 13.78 mmol) was added. The mixture was stirred at RT for 2 hours and additionally at 70° C. for 30 minutes and thereafter at reflux for 1 hour. The reaction mixture was stirred at RT overnight whereafter the precipitated yellow crystals were isolated and washed with toluene. Yield of title compound was 1.3 g including solvent content.

c) 1-aminocarbonylmethyl-1H-indole-2,3-dione.

The product prepared under b) was dissolved in dry THF (50 ml) and to the solution was added liquid NH$_3$. The resulting mixture was stirred overnight at RT. The precipitated orange crystals were isolated and were washed with water. Yield of title compound was 0.46 g.

d) 1-cyanomethyl-1H-indole-2,3-dione.

Triphenylphosphine (0.75 g, 2.84 mmol) was dissolved in methylenechloride and to the solution was added dropwise to Br$_2$ (0.15 ml, 2.84 mmol) in methylenechloride (20 ml). To this mixture the product prepared under c) was added, and thereafter triethylamine (0.8 ml, 5.68 mmol) was added dropwise. The mixture was stirred for 30 minutes. The reaction mixture was evaporated in vacuo and the residue was taken up in ether. The precipitate from this mixture was filtered off and the ether solution was washed with water and dried (MgSO$_4$). The ether solution was evaporated in vacuo and the residue was washed with isopropanol. Yield of title compound was 0.11 g. M.p. 125°–128° C.

e) 1-(acetamideoxime-2-yl)-1H-indole-2,3-dione-3-oxime.

The product prepared under d) (90 mg, 0.48 mmol), hydroxylamine hydrochloride (70 mg, 1.06 mmol), potassium carbonate (150 mg, 1.06 mmol) and methanol (10 ml) were mixed and the mixture was stirred at RT overnight. The reaction mixture was evaporated in vacuo. The residue was washed with water containing small amounts of acetic acid. Yield of title compound was 70 mg. M.p. 227°–229° C.

It is thus seen that the present invention provides a new and convenient process for the production of indole-2,3- dione-3-oxime compounds, certain novel indole-2,3-dione-3-oxime compounds which are useful as excitatory amino acid antagonists, pharmaceutical-compositions useful as excitatory amino acid antagonists comprising certain indole-2,3-dione-3-oxime compounds, and a method of antagonizing the biological effects of excitatory amino acids in a subject in need thereof comprising the step of administering certain indole-2,3-dione-3-oxime compounds or a pharmaceutical composition comprising the same together with a pharmaceutically-acceptable diluent or carrier, all having the foregoing characteristics and advantages.

It is to be understood that the invention is not to be limited to the exact details of operation, or to the exact methods, procedures, or embodiments shown and described, as obvious modifications and equivalents will be apparent to one skilled in the art, and the invention is therefore to be limited only by the full scope of the appended claims.

We claim:

1. A method of antagonizing the biological effects of an excitatory amino acid of a subject in need of such antagonization comprising the step of administering to said subject an effective excitatory amino acid antagonizing amount of an indole-2,3-dione-3-oxime compound having the formula

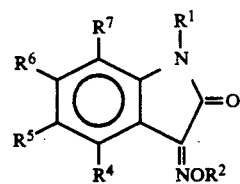

wherein
R$^1$ is hydrogen, C$_{1-6}$-alkyl which may be branched, C$_{3-7}$-cycloalkyl, benzyl, and phenyl carboxylic acid acyl, hydroxy, C$_{1-6}$-alkoxy, CH$_2$CO$_2$R' wherein R' is hydrogen or C$_{1-6}$-alkyl which may be branched, CH$_2$CN, CH$_2$CONR$^{IV}$R$^V$ wherein R$^{IV}$ and R$^V$ independently are hydrogen or C$_{1-6}$-alkyl, or CH$_2$C(=NOH)NH$_2$;
R$^2$ is hydrogen, benzyl, C$_{1-6}$-alkyl which may be branched, or C$_{3-7}$-cycloalkyl;
R$^4$, R$^5$, R$^6$, R$^7$ independently are hydrogen, C$_{1-6}$-alkyl which may be branched, phenyl, halogen, C$_{1-6}$-alkoxy, NO$_2$, CN, CF$_3$, OCF$_3$, or SO$_2$NR''R''' wherein R'' and R''' independently are hydrogen, aralkoxy, aralkyl, or C$_{1-6}$-alkyl; or R$^6$ and R$^7$ together form an additional 4 to 7 membered ring which may be aromatic or partially saturated and which may be substituted with halogen, NO$_2$, CF$_3$, CN, OCF$_3$, or SO$_2$NR''R''' wherein R'' and R''' independently are hydrogen, aralkoxy, aralkyl, or C$_{1-6}$-alkyl, and R$^4$ and R$^5$ have the meanings set forth above.

2. A method according to claim 1 wherein at least one of R$^4$, R$^5$, R$^6$ or R$^7$ is NO$_2$, CF$_3$, CN, SO$_2$NR''R''', or halogen and R$^1$, R$^2$, R$^4$, R$^5$, R$^6$, R$^7$, R'', and R''' otherwise have the meanings set forth in claim 1.

3. A method according to claim 1 wherein R$^5$ is NO$_2$, F, CF$_3$, OCF$_3$, or CN.

4. A method of antagonizing the biological effects of an excitatory amino acid according to claim 1, wherein the compound is administered in the form of a pharmaceutical composition thereof, in which it is present together with a pharmaceutically acceptable carrier or diluent.

5. A method of antagonizing the biological effects of an excitatory amino acid according claim 2, wherein the compound is administered in the form of a pharmaceutical composition thereof, in which it is present together with a pharmaceutically acceptable carrier or diluent.

6. A pharmaceutical composition for use in antagonizing the biological effects of an excitatory amino acid of a subject in need of such antagonization comprising an effective excitatory amino acid antagonizing amount of a compound having the formula

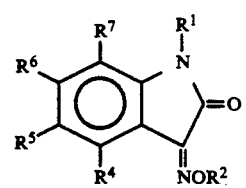

wherein R$^1$ is hydrogen; R$^2$ is hydrogen, benzyl, C$_{1-6}$-alkyl which may be branched, or C$_{3-7}$-cycloalkyl; R$^4$, R$^5$, R$^6$, R$^7$ independently are hydrogen, C$_{1-6}$-alkyl which may be branched, phenyl, halogen, C$_{1-6}$-alkoxy, NO$_2$, CF$_3$, OCF$_3$, CN, or SO$_2$NR''R''' wherein R'' and R''' independently are hydrogen, aralkoxy, aralkyl, or $C_{1-6}$-alkyl, or $R^6$ and $R^7$ together form an additional 4 to 7 membered ring which may be aromatic or partially saturated and which may be substituted with halogen, $NO_2$, $CF_3$, $CN$, $OCF_3$, or $SO_2NR''R'''$ wherein R'' and R''' independently are hydrogen, aralkoxy, aralkyl, or $C_{1-6}$-alkyl, and $R^4$ and $R^5$ have the meanings set forth above, at least one of $R^4$, $R^6$ and $R^7$ are other than hydrogen when $R^5$ is not other than H, Cl or Br;

or $R^1$ is $C_{1-6}$-alkyl which may be branched, $C_{3-7}$-cycloalkyl, benzyl, phenyl, carboxylic acid acyl, hydroxy, $C_{1-6}$-alkoxy, $CH_2CO_2R'$ wherein R' is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, $CH_2C(=NOH)NH_2$; $R^2$ is hydrogen, benzyl, $C_{1-6}$-alkyl which may be branched, or $C_{3-7}$-cycloalkyl;

$R^4$, $R^5$, $R^6$, $R^7$ independently are hydrogen, $C_{1-6}$-alkyl which may be branched, phenyl, halogen, $C_{1-6}$-alkoxy, $NO_2$, $CF_3$, $OCF_3$, $CN$, or $SO_2NR''R'''$ wherein R'' and R''' independently are hydrogen, aralkoxy, aralkyl, or $C_{1-6}$-alkyl, or $R^6$ and $R^7$ together form an additional 4 to 7 membered ring which may be aromatic or partially saturated and which may be substituted with halogen, $NO_2$, $CF_3$, $CN$, $OCF_3$, or $SO_2NR''R'''$ wherein R'' and R''' independently are hydrogen, aralkoxy, aralkyl, or $C_{1-6}$-alkyl, and $R^4$ and $R^5$ have the meanings set forth above, at least one of $R^4$, $R^5$, $R^6$ and $R^7$ are other than hydrogen when $R^1$ is methyl, at least one of $R^4$ and $R^5$ are other than hydrogen when $R^1$ is phenyl, and at least one of $R^4$ and $R^5$ are other than hydrogen when $R^6$ and $R^7$ together form an additional benzene ring.

7. A method of antagonizing the biological effects of an excitatory amino acid of a subject in need thereof comprising the step of administering to said subject a pharmaceutical composition according to claim 6.

8. A compound having the formula

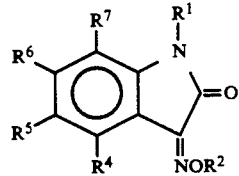

wherein $R^1$ is $C_{1-6}$-alkyl which may be branched, $C_{3-7}$-cycloalkyl, carboxylic acid acyl, hydroxy, $C_{1-6}$-alkoxy, $CH_2CO_2R'$ wherein R' is hydrogen or $C_{1-6}$-alkyl which may be branched, $CH_2CN$, $CH_2CONR^{IV}R^V$ wherein $R^{IV}$ and $R^V$ independently are hydrogen or $C_{1-6}$-alkyl, or $CH_2C(=NOH)NH_2$;

$R^2$ is hydrogen, benzyl, $C_{1-6}$-alkyl which may be branched, or $C_{3-7}$-cycloalkyl;

$R^5$ is $NO_2$, F, CN, $OCF_3$, $CF_3$, or $SO_2NR''R'''$ wherein R'' and R''' independently are hydrogen, aralkoxy, aralkyl or $C_{1-6}$-alkyl; and $R^4$, $R^6$, $R^7$ independently are hydrogen, $C_{1-6}$-alkyl which may be branched, phenyl, halogen, $C_{1-6}$-alkoxy, $NO_2$, $OCF_3$, $CF_3$, CN, or $SO_2NR''R'''$ wherein R'' and R''' independently are hydrogen, aralkoxy, aralkyl or $C_{1-6}$-alkyl, or $R^6$ and $R^7$ together form an additional 4 to 7 membered ring which may be aromatic or partially saturated and which may be substituted with halogen, $NO_2$, $CF_3$, CN, $OCF_3$, or $SO_2NR''R'''$ wherein R'' and R''' independently are hydrogen, aralkoxy, aralkyl, or $C_{1-6}$-alkyl, and $R^4$ has the meaning set forth above.

9. A compound having the formula

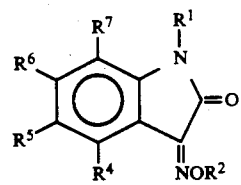

wherein
$R^1$ is hydrogen,
$R^2$ is hydrogen, benzyl, $C_{1-6}$-alkyl which may be branched, or $C_{3-7}$-cycloalkyl;
$R^5$ is $NO_2$, F, $CF_3$, CN, $OCF_3$, or $SO_2NR''R'''$ wherein R'' and R''' independently are hydrogen, aralkoxy, aralkyl or $C_{1-6}$-alkyl; and
$R^4$, $R^6$, $R^7$ independently are hydrogen, $C_{1-6}$-alkyl which may be branched, phenyl, halogen, $C_{1-6}$-alkoxy, $NO_2$, $CF_3$, $OCF_3$, CN, or $SO_2NR''R'''$ wherein R'' and R''' independently are hydrogen, aralkoxy, aralkyl or $C_{1-6}$-alkyl, or $R^6$ and $R^7$ together form an additional 4 to 7 membered ring which may be aromatic or partially saturated and which may be substituted with halogen, $NO_2$, $CF_3$, CN, $OCF_3$, or $SO_2NR''R'''$ wherein R'' and R''' independently are hydrogen, aralkyl, aralkoxy or $C_{1-6}$-alkyl, and $R^4$ has the meaning set forth above; and that $R^5$ is different from $NO_2$ and F when $R^1$, $R^4$, $R^6$ and $R^7$ are not other than hydrogen and $R^2$ is hydrogen or benzyl; and that $R^5$ is different from $NO_2$ when $R^1$, $R^2$, $R^4$ and $R^6$ are other than hydrogen and $R^7$ is $NO_2$.

10. A compound according to claim 8 or 9 wherein $R^4$ and $R^5$ independently are hydrogen, F, $NO_2$, CN, $CF_3$, $OCF_3$, or $SO_2NR''R'''$ wherein R'' and R''' independently are hydrogen, aralkoxy, aralkyl or $C_{1-6}$-alkyl, and wherein $R^6$ and $R^7$ together form an additional 4 to 7 membered ring which may be aromatic or partially saturated and which may be substituted with halogen, $NO_2$, $CF_3$, $OCF_3$, CN, or $SO_2NR''R'''$ wherein R'' and R''' independently are hydrogen, aralkoxy, aralkyl or $C_{1-6}$-alkyl.

11. A compound according to claim 10 wherein the additional ring formed by $R^6$ and $R^7$ is substituted with halogen, $NO_2$, $CF_3$, CN or $SO_2NR''R'''$ wherein R'' and R''' independently are hydrogen, aralkoxy, aralkyl or $C_{1-6}$-alkyl.

12. A compound of claim 9, which is 6-(N-methylsulphamoyl)-5-nitro-1H-benz[g]indole-2,3-dione-3-oxime.

13. A compound of claim 8, which is 5,7-dinitro-1-methyl-1H-indole-2,3-dione-3-(O-methyloxime).

14. A compound of claim 9, which is 5-(N-benzyloxysulphamoyl)-1H-6,7,8,9-tetrahydro-benz[g]indole-2,3-dione-3-oxime.

15. A method of treating a central nervous system disorder in a subject in need of such treatment, comprising the step of administering to said subject an effective amount of a compound having the formula

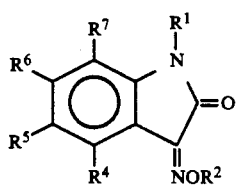

wherein $R^1$ is hydrogen, $C_{1-6}$-alkyl which may be branched, $C_{1-6}$-cycloalkyl, benzyl, phenyl carboxylic acid acyl, hydroxy, $C_{1-6}$-alkoxy, $CH_2CO_2R'$ wherein $R'$ is hydrogen or $C_{1-6}$-alkyl which may be branched, $CH_2CN$, $CH_2CONR^{IV}R^{V}$ wherein $R^{IV}$ and $R^{V}$ independently are hydrogen or $C_{1-6}$-alkyl, or
$CH_2C(=NOH)NH_2$; $R^2$ is hydrogen, benzyl, $C_{1-6}$-alkyl which may be branched, or $C_{3-7}$-cycloalkyl; $R^5$ is $NO_2$, F, $CF_3$, $OCF_3$, CN, or $SO_2NR''R'''$ wherein $R''$ and $R'''$ independently are hydrogen, aralkyl, aralkoxy or $C_{1-6}$-alkyl; and $R^4$, $R^6$, $R^7$ independently are hydrogen, $C_{1-6}$-alkyl which may be branched, phenyl, halogen, $C_{1-6}$-alkoxy, $NO_2$, CN, $CF_3$, $OCF_3$, or $SO_2NR''R'''$ wherein $R''$ and $R'''$ independently are hydrogen, aralkoxy, aralkyl or $C_{1-6}$-alkyl, or $R^6$ and $R^7$ together form an additional 4 to 7 membered ring which may be aromatic or partially saturated and which may be substituted with halogen, $NO_2$, $CF_3$, CN, $OCF_3$, or $SO_2NR''R'''$ wherein $R''$ and $R'''$ independently are hydrogen, aralkoxy, aralkyl or $C_{1-6}$-alkyl, and $R^4$ has the meaning set forth above; and that $R^5$ is different from $NO_2$ and F when $R^1$, $R^4$, $R^6$ and $R^7$ are hydrogen and $R^2$ is hydrogen or benzyl; and that $R^5$ is different from $NO_2$ when $R^1$, $R^2$, $R^4$ and $R^6$ are hydrogen and $R^7$ is $NO_2$.

16. The method of claim 15 wherein at least one of $R^4$, $R^5$, $R^6$ or $R^7$ is $NO_2$, $CF_3$, CN, $OCF_3$, $SO_2NR''R'''$, or halogen.

* * * * *

UNITED STATES PATENT AND TRADEMARK OFFICE
CERTIFICATE OF CORRECTION

PATENT NO. : 5,198,461

DATED : Mar. 30, 1993

INVENTOR(S) : Frank Wátjen, Jorgen Drejer, Leif H. Jensen

It is certified that error appears in the above-indentified patent and that said Letters Patent is hereby corrected as shown below:

Column 1, approximately line 32; "87," should read -- 37, --.
Column 2, line 48; "$R^1$, and" should read --R   --"R" and" --.
Column 3, approximately line 42; "$C_3$," should read
       -- $CF_3$, --

Column 5, line 17,18; "$CH^1-_6C$" should read -- $CH_2C$ --.
Column 8, line 4 and 5; move the bracket "[" from the end of
     line 4 to the beginning of line 5 and insert before "g".
Column 8, line 6 and 7; move the bracket "[" from the end of
     line 6 to the beginning of line 7 and insert before "g".
Column 8, line 67; "20 pg" should read -- µg --.
Column 9, line 8; "give" should read -- given --.
Column 10, line 59; "hu 2) Martinet," should read
       -- [2)]Martinet, --.
Column 11, line 42; "chlorid" should read -- chloric --.
Column 11, approximately lines 57, 58; move the opening bracket
     "[" from the end of line 57 to the beginning of line 58
before "g]".
Column 13, line 12; " (0-methyl-oxime)" should read --(O-methyloxime)--

Column 14, line 19; "5-(n-" should read -- 5-(N- --.
Column 18, approximately line  35; delete "not other than".

UNITED STATES PATENT AND TRADEMARK OFFICE
CERTIFICATE OF CORRECTION

PATENT NO. : 5,198,461
DATED : Mar. 30, 1993
INVENTOR(S) : Frank Wátjen, Jorgen Drejer, Leif H. Jensen It is certified that error appears in the above-indentified patent and that said Letters Patent is hereby corrected as shown below:

Column 18, approximately line 37; delete "other than".
    (Cl. 9, old Cl. 10 - R&A 1-15-92, P. 2)
Column 19, line 11; "$C_{1-6}$," should read -- $CF_{3-7}$ --.

Signed and Sealed this

Twelfth Day of September, 1995

*Attest:*

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,198,461         Page 1 of 2
DATED      : Mar. 30, 1993
INVENTOR(S) : Frank Wátjen, Jorgen Drejer, Leif H. Jensen It is certified that error appears in the above-indentified patent and that said Letters Patent is hereby corrected as shown below:

Column 1, approximately line 32; "87," should read -- 37, --.
Column 2, line 48; "R'. and" should read -- "R'' and" -- .
Column 3, approximately line 42; "C$_3$," should read -- CF$_3$, --
Column 3, line 6; "CF$^3$" should read -- CF$_3$ --.
Column 5, line 17,18; "CH$^1$-$_6$C" should read -- CH$_2$C --.
Column 8, line 4 and 5; move the bracket "[" from the end of line 4 to the beginning of line 5 and insert before "g".
Column 8, line 6 and 7; move the bracket "[" from the end of line 6 to the beginning of line 7 and insert before "g".
Column 8, line 67; "20 pg" should read -- µg --.
Column 9, line 8; "give" should read -- given --.
Column 10, line 59; "hu 2) Martinet," should read -- $^{2)}$Martinet, --.
Column 11, line 42; "chlorid" should read -- chloric --.
Column 11, approximately lines 57, 58; move the opening bracket "[" from the end of line 57 to the beginning of line 58 before "g]".
Column 13, line 12; "(Omethyloxime)," should read -- (O-methyl-oxime), --.
Column 14, line 19; "5-(n-" should read -- 5-(N- --.
Column 18, approximately line 35; delete "not other than".

UNITED STATES PATENT AND TRADEMARK OFFICE
CERTIFICATE OF CORRECTION

PATENT NO. : 5,198,461
DATED : Mar. 30, 1993
INVENTOR(S) : Frank Wåtjen, Jorgen Drejer, Leif H. Jensen It is certified that error appears in the above-indentified patent and that said Letters Patent is hereby corrected as shown below:

Column 18, approximately line 37; delete "other than".

Column 19, line 11; "$C_{1-6}$," should read -- $C_{3-7}$ --.

This certificate supersedes Certificate of Correction issued September 12, 1995.

Signed and Sealed this

Nineteenth Day of December, 1995

Attest:

BRUCE LEHMAN

Attesting Officer

Commissioner of Patents and Trademarks